United States Patent [19]

Broucek

[11] 4,363,317
[45] Dec. 14, 1982

[54] WATERTIGHT CAST COVER

[76] Inventor: Daniel M. Broucek, 3010 Shaffer Rd., SE., Grand Rapids, Mich. 49508

[21] Appl. No.: 254,971

[22] Filed: Apr. 16, 1981

[51] Int. Cl.³ .............................................. A61F 13/00
[52] U.S. Cl. ...................................................... 128/82
[58] Field of Search ................. 128/82, DIG. 15, 165, 128/157

[56] References Cited

U.S. PATENT DOCUMENTS

| | | |
|---|---|---|
| 1,156,238 | 10/1915 | Litchfield . |
| 1,246,948 | 11/1917 | Sears . |
| 1,349,206 | 8/1920 | Jeffers . |
| 1,980,486 | 11/1934 | King et al. . |
| 2,072,483 | 3/1937 | Naundorf . |
| 2,229,575 | 1/1941 | Kaplan .............................. 128/82 X |
| 2,244,871 | 6/1941 | Guinzburg . |
| 2,582,648 | 1/1952 | Mowbray . |
| 3,026,526 | 3/1962 | Montrose . |
| 3,113,319 | 12/1963 | Vail . |
| 3,324,580 | 6/1967 | Baxter .............................. 128/82 X |
| 3,488,774 | 1/1970 | Abbott . |
| 3,735,759 | 5/1973 | MacKay . |
| 3,741,203 | 6/1973 | Liman . |
| 3,747,125 | 7/1973 | Goldman et al. . |
| 3,778,846 | 12/1973 | Norie . |
| 3,785,374 | 1/1974 | Lipson . |
| 3,820,533 | 6/1974 | Jones . |
| 3,906,941 | 9/1975 | Cook, Jr. . |
| 4,036,220 | 7/1977 | Bellasalma . |
| 4,043,326 | 8/1977 | Little et al. . |
| 4,085,746 | 4/1978 | Castiglia ..................... 128/DIG. 15 |
| 4,254,765 | 3/1981 | Brown et al. . |

Primary Examiner—John D. Yasko
Attorney, Agent, or Firm—Price, Heneveld, Huizenga & Cooper

[57] ABSTRACT

A watertight cast cover for protecting a cast, bandage or the like includes an elongated, generally tubular waterproof member having a closed end and an open end. An adjustable resilient sealing band extends around the periphery of the open end of the member. The band includes overlapping ends, one end of which defines a flap. The flap and band may be stretched to form a seal with the user's limb and the flap is securable to the band.

8 Claims, 7 Drawing Figures

WATERTIGHT CAST COVER

BACKGROUND OF THE INVENTION

The present invention relates to coverings and more particularly to a unique waterproof cover for protecting a cast, bandage or the like on the user's limb.

A problem experienced by an individual having a cast, bandage or the like on an arm or leg involves keeping the limb dry when bathing. Water may damage the bandage or cast and can cause discomfort. Heretofore, various proposals have been made to cover the limb to prevent it from getting wet when the user takes a bath or shower. One common approach is to place the limb in a plastic type bag and seal the open end with a rubber band. This arrangement does not always provide an adequate seal. The seal is dependent upon the particular size of the rubber band used and the degree of care used by the individual in folding over the excess material at the upper end of the bag when applying the rubber band. If a particularly tight rubber band is used, the circulation to the limb may be restricted. This can produce discomfort.

Another approach is disclosed in U.S. Pat. No. 2,224,871, entitled Waterproof Protective Device and issued on June 10, 1941, to Guinzburg. The device disclosed in this patent includes an elongated, waterproof tubular member within which the limb may be placed. The tubular member defines an integral sealing flange. The flange is an endless band of soft and elastic sheet rubber or latex which extends completely around the tubular member interior adjacent an upper end. An adequate seal may not always be provided with such structure. The device may not be dimensioned properly for the individual. No adjustability is provided to compensate for size differences.

A still further example of a cast cover may be found in U.S. Pat. No. 4,043,326, entitled Waterproof Cast Protector and issued on Aug. 23, 1977, to Little et al. This patent discloses a unitary, flexible cover having a receptacle portion at one end and a sealing portion at the opposite end. The sealing portion is defined by a rib of covering material formed by rolling the generally tubular shaped device over itself. The limb is inserted into the article and the sealing portion unrolled onto the cast, bandage or the like until it reaches a position above same on the individual's limb. The relaxed diameter of the interior of the sealing portion is dimensioned to be less than the general diameter of the individual's limb. No adjustability is provided and various size coverings have to be manufactured to accommodate children and adults of different ages and sizes.

A need exists for a reusable, waterproof cover to protect a cast, bandage or the like and which cover is adjustable to insure an adequate and comfortable seal with the range of sizes of individuals who would have a need to use the cover.

SUMMARY OF THE INVENTION

In accordance with the present invention, the aforementioned needs are substantially fulfilled. Essentially, a watertight cover is provided which includes an elongated, generally tubular waterproof member. The member has a closed lower end and an open top and is dimensioned to loosely receive an individual's limb. An adjustable, resilient seal means extends around the periphery of the open top of the member. The seal means provides a seal with the limb of the user and is adjustable in circumference to accommodate different size individuals and to insure a comfortable seal.

In narrower aspects of the invention, the seal means includes an elongated, elastic band. The band has a length which is greater than the periphery of the open top end of the tubular member. As a result, the band includes overlapping ends. A securement means is provided to secure a free flap of the band after adjustment. The band includes a first lateral edge which is joined to the periphery of the tubular member and a second lateral edge. In the area of the band where the ends overlap, the second lateral edge is angled downwardly towards the open top to define a cutout portion. This permits the band to be folded on itself during adjustment and insures that a suitable seal is obtained. The elongated tubular member may include a foot portion to receive the foot of the user. In the alternative, the member may be of relatively constant diameter and used to cover an arm.

The cover is dimensioned to loosely receive the limb of the user to reduce any discomfort associated with use of the device. The adjustable seal insures that the cover may be used with different size individuals and eliminates problems heretofore experienced with excessive tightness and resulting restriction of circulation to the limb.

BRIEF DESCRIPTION OF THE DRAWINGS

FIG. 7 is a perspective view showing an alternative embodiment of the present invention which is adapted to protect an arm cast, bandage or the like.

DETAILED DESCRIPTION OF THE PREFERRED EMBODIMENT

Figure 1:
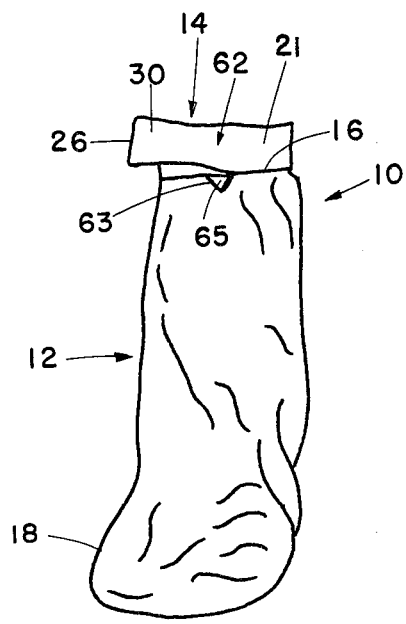
FIG. 1 is a plan view of a watertight cover in accordance with the present invention.

The preferred embodiment of the watertight cover in accordance with the present invention is illustrated in FIG. 1 and generally designated 10. Cover 10 includes an elongated, generally tubular member 12 and an adjustable sealing means 14.

Tubular member 12 is formed from a waterproof material such as rubber or vinyl. Member 12 includes an open upper or top end 16 and a closed bottom or lower end 18. It is presently preferred that the tubular member be formed from a sheet of waterproof material the edges of which are joined by heat sealing to define the open top and closed bottom. The seam defined by the heat sealing is designated 17 in FIGS. 2 and 3. Tubular member 12 is dimensioned to provide more than enough volume to receive the limb and cast of the user. A "loose fit" is desired to prevent any discomfort as has heretofore been experienced with prior cast protectors. The volume also adapts the device to individuals of different sizes.

Figure 2:
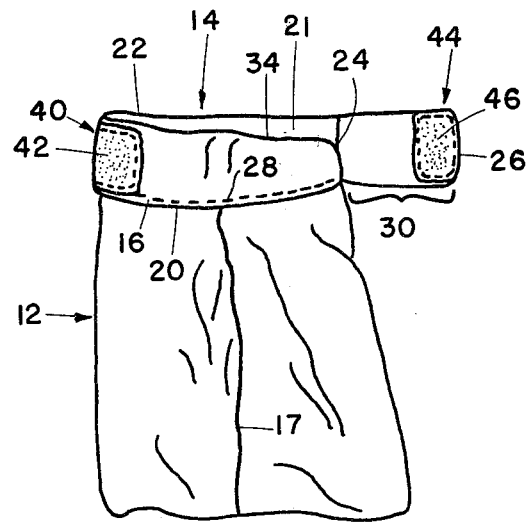
FIG. 2 is an enlarged fragmentary plan view of the upper portion of the cover showing the adjustable seal.
Figure 3:
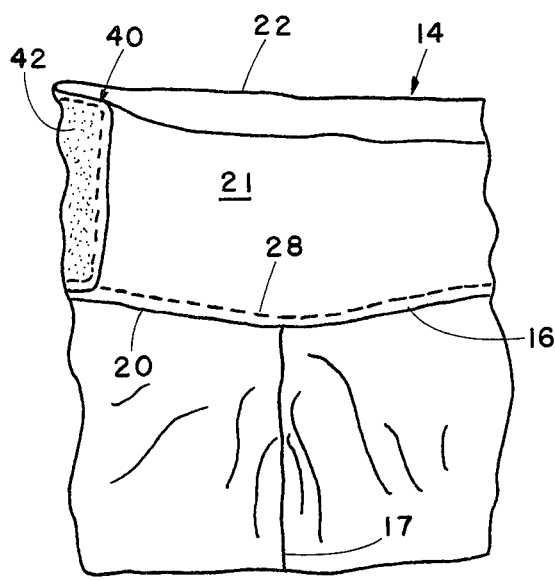
FIG. 3 is a greatly enlarged fragmentary view of the upper portion of the cover showing a portion of the seal.

As seen in FIGS. 2 and 3, sealing means 14 includes an elongated resilient band 21 having a first lateral edge 20 and a second lateral edge 22. The band further includes ends 24 and 26 (FIG. 2). As is clear from FIG. 2, the band has a longitudinal dimension which is greater than the circumference or periphery of the upper end 16 of tubular member 12. The band is secured to the upper end of the tubular member by a suitable means such as by stitching 28 shown in FIGS. 2 and 3. When secured to the tubular member, end 24 is fixed and end 26 is free so that the band defines an elongated flap portion 30 which can overlap end 24. Band 14 is an elastic member and may be formed from gum rubber, latex or like material. The band is elastic or stretchable to insure that an adequate seal is provided with the limb of the user.

As seen in FIG. 2, lateral edge 22 of the band defines an angled portion 34. Portion 34 is angled downwardly towards edge 20 or the top 16 of member 12. The band in effect defines a "cutout" portion which provides space for the band material to be folded, as explained below.

Further, as seen in FIG. 2, a reusable attachment or securement means is provided for securing the flap portion 30 to the band. In the embodiment illustrated, the securement means includes a first component or member 40 which is secured to the band and extends longitudinally and transversely thereof. Component 40 defines an exposed nap 42. The securement means further includes a second component 44 which is carried on an inner surface of flap portion 30 adjacent free end 26. Component 44 defines an exposed nap 46.

Nap surfaces 42, 46 in the presently preferred embodiment comprise interconnecting male and female portions. One surface includes a plurality of loops and the other surface includes a plurality of hooks. When the surfaces are pressed into contact, the hooks interconnect with the loops to positively yet removably secure flap portion 30 to the band. The hook and loop fasteners are of the general type illustrated and described in U.S. Pat. No. 2,717,437, entitled Velvet Type Fabric and Method of Producing Same and issued on Sept. 13, 1955, to Mestral and U.S. Pat. No. 3,009,235, entitled Separable Fastening Device and issued on Nov. 21, 1961, to Mestral. Components 40 and 44 may be purchased in strip form, cut and secured to the band by any suitable means as by stitching or with a suitable adhesive. The attachment means is a commercially available item. In the alternative, other attachment means besides that illustrated and described could be employed. For example, reusable fasteners are available which include a member or component defining an exposed nap and a second component defining a plurality of button-like projections. The button-like projections interconnect with the exposed nap in the same basic manner as the hook and loop fasteners described. Also, snap fasteners might be usable, although the full range of adjustment would not result.

In the presently existing embodiment of the cast protector in accordance with the present invention, the elongated tubular member 12 has an overall length of approximately 3 feet and a maximum width of approximately 1½ feet. The lower or closed end portion 18 defines a large "boot" or foot receiving portion. This embodiment is primarily adapted to protect a leg cast on the user. The upper open top 16 has a circumference or peripheral length dimension of approximately 17 inches. The tubular member is formed from a thin sheet of vinyl which is cut to the "stocking" configuration and then heat sealed at its lateral edges. The heat seal is schematically shown in FIG. 3 and designated 17.

The sealing means is defined by an elongated band of gum rubber having a length dimension of approximately 26 inches and a maximum width dimension of approximately 4 inches. When secured to the open top, the flap 30 has a dimension longitudinally of approximately 9 inches. Angled lateral edge portion 34 extends downwardly towards lateral edge 20 at an angle of approximately 45°. Lateral edge 24 has a length dimension of approximately 7 inches. The elastic band in the presently existing embodiment is stitched to the open top of member 12. Component 40 of the securement means is secured to the band at a point beginning approximately 12 inches from the fixed end 24. The component 40 extends across substantially the entire transverse or width dimension of the band and has a length dimension of approximately 8 inches. This provides a significant degree of adjustability for the band. Component 42 extends across substantially the entire transverse or width dimension of flap 30 and has a length dimension of approximately 2 inches. The components are secured to the band by stitching.

Figure 4:
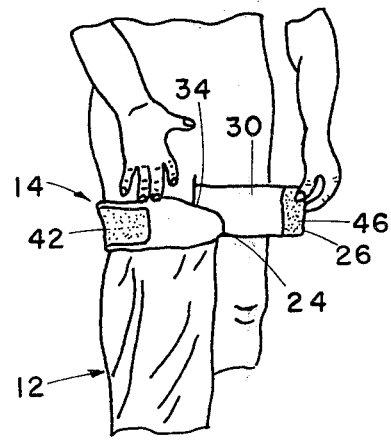
FIGS. 4–6 illustrate the manner of using the cover to protect a lower leg cast.
Figure 5:
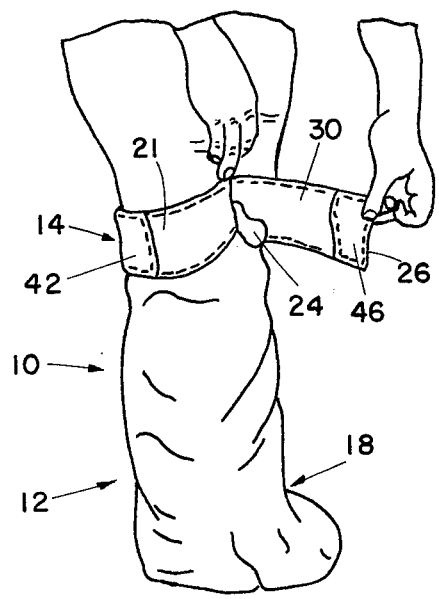
Figure 6:
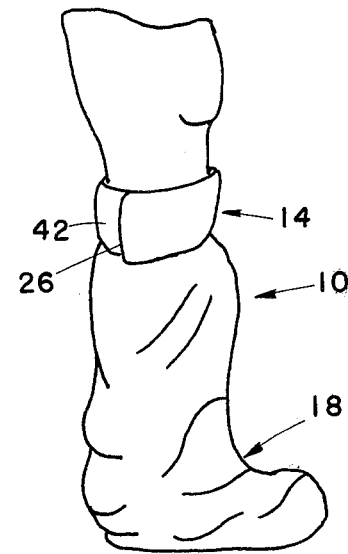

The manner of using the protective cover in accordance with the present invention is illustrated in FIGS. 4, 5 and 6. As shown, the top of the cover is opened and the user inserts the limb to be protected. In the embodiment shown, the device is used to protect a leg cast. The user then, as shown in FIG. 5, holds the elastic band 21 against the limb and grasps the free end 26 of the band. The flap is moved so that it will overlap the band. The band material may be folded upon itself, as shown in FIG. 5. By stretching the flap and hence the elastic band, a seal is provided between the band interior surface and the limb of the user. When pulled tight to insure an adequate seal, the user then places exposed nap 46 of component 44 on flap 30 against exposed nap 42 on the fixed component 40. The resilience and elasticity of the band insures that a seal is obtained. Since component 40 extends over a length of the band, a significant degree of adjustment is provided. Further, providing the cutout portion permits the band to be folded and the folded portion is completely covered by the sealing flap 30. If the cutout were eliminated and the band was the same transverse dimension throughout its entire length, the folded portions could extend beyond the upper lateral surface of the flap or be "open" from above. This could provide a passage for moisture into the covering. The cutout portion reduces the care needed to obtain a good seal.

Also, as shown in FIG. 1, the top edge portion of member 12 may be provided with a gusset 62. Gusset 62 is a V-shaped notch 63 cut in the member. Extra material 65 dimensioned greater than the notch is joined to the edges of the notch. The gusset 62 permits the upper edge of the member 12 to be folded upon itself straight across. This may also insure a proper seal.

Figure 7:
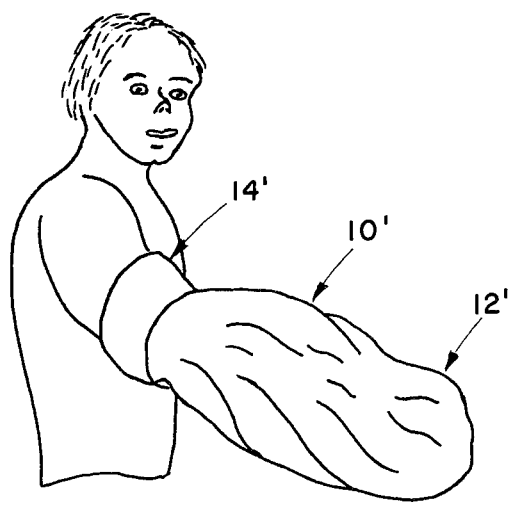

As shown in FIG. 7, the cover in accordance with the present invention is readily usable to protect a cast, bandage or the like on the arm, wrist or hand of the individual. The arm protector, designated 10' in FIG. 7, would preferably be dimensioned smaller than the leg cast protector described above. Protector 10' includes a tubular member 12' and a seal means 14'. The foot receiving portion of embodiment 10 would, of course, be eliminated. Member 12' would be of essentially constant diameter throughout its length. Seal means 14' is formed in precisely the same manner described above with respect to the seal means 14.

The protective cover in accordance with the present invention loosely receives the injured limb. This permits the user to easily insert the limb into the cover. Size differences are readily accommodated. The seal is fully adjustable to accommodate different size individuals. The adjustability also permits the user to position the flap so that the seal is only tight enough to prevent water leakage without having an adverse effect on circulation to the limb. This increases the comfort of the individual while bathing.

In view of the foregoing description, those of ordinary skill in the art will undoubtedly envision various modifications which would not depart from the inventive concepts disclosed herein. For example, as mentioned above, detachable and reusable securement means other than the hook and loop fasteners could be employed. Further, it is believed that the elastic band forming the seal means could be made as an integral portion of the tubular member. For example, the entire device could be fabricated from an elasticized vinyl material. This would eliminate one step in the manufacturing process, namely, attachment of the elastic band to the tubular member. Also, the elastic band may include integral reinforcement along the portion where it joins member 12 and in the areas of the attachment means. Such reinforcement may be molded into the band and could take the form of a mesh cloth. Therefore, it is expressly intended that the above description should be considered only as that of the preferred embodiment. The true spirit and scope of the present invention may be determined by reference to the appended claims.

The embodiments of the invention in which an exclusive property or privilege is claimed are defined as follows:

1. A watertight cover for protecting a cast, bandage or the like on an individual's limb, said cover comprising:
   an elongated, generally tubular waterproof member having an open end, said member dimensioned to receive the limb of the individual; and
   adjustable, resilient seal means joined to and extending around the periphery of said open end of said member for sealing the open end of said member to the limb, said seal means being adjustable in circumference to accommodate different size individuals and insure a comfortable seal to the limb, said adjustable seal means being an elongated elastic band having a first lateral edge extending around and joined to substantially the entire periphery of said open end, said band including a fixed end portion which defines an upper lateral edge, a portion of said upper lateral edge being angled toward the periphery of said open end, said band having a free end portion overlapping the fixed end portion thereof, whereby said free end portion may be stretched over said fixed end portion and said band at said fixed end portion may be folded upon itself, thereby insuring that an effective leak proof seal may be obtained, and wherein said seal further includes detachable securing means for detachably securing said free end portion in overlapping relationship with said fixed end portion.

2. A watertight cast as defined by claim 1 wherein said tubular waterproof member is formed from a sheet of flexible waterproof material which is cut and sealed along a pair of edges to define a closed end and said open end.

3. A watertight cast as defined by claim 2 wherein said tubular member includes a gusset adjacent its open end.

4. A watertight cast as defined by claim 2 wherein said securing means comprises:
   a first component on said band adjacent said fixed end portion; and
   a second component on said free end portion, said components including interengaging members for detachably securing said components together.

5. A watertight cast as defined by claim 6 wherein said interengaging members of said components include each of said components defining an exposed nap, said exposed naps interlocking when pressed together.

6. A watertight cast as defined by claim 2 wherein said elastic band is a separate member joined to the open end of said elongated member.

7. A watertight cast as defined by claim 6 wherein said detachable securing means comprises:
   a first component defining an exposed nap, said first component being secured to said band between its ends and positioned to be overlapped by said one of said ends; and
   a second component definining an exposed nap, said second component being secured to said one of said ends, said exposed naps of said components interlocking when pressed together.

8. A watertight cast as defined by claim 7 wherein said tubular member includes a closed foot receiving portion.

* * * * *

UNITED STATES PATENT AND TRADEMARK OFFICE
CERTIFICATE OF CORRECTION

PATENT NO. : 4,363,317

DATED : December 14, 1982

INVENTOR(S) : Daniel M. Broucek

It is certified that error appears in the above-identified patent and that said Letters Patent is hereby corrected as shown below:

Column 6, claim 5, line 27:

"claim 6" should be --claim 4--.

Signed and Sealed this

*Twenty-second* Day of *March 1983*

[SEAL]

*Attest:*

GERALD J. MOSSINGHOFF

*Attesting Officer*     *Commissioner of Patents and Trademarks*